United States Patent [19]

Wehrli

[11] 3,941,852
[45] Mar. 2, 1976

[54] SYNTHESIS OF 2-METHYL-3-BUTEN-2-OL
[75] Inventor: Pius Anton Wehrli, North Caldwell, N.J.
[73] Assignee: Hoffmann-La Roche Inc., Nutley, N.J.
[22] Filed: June 19, 1974
[21] Appl. No.: 480,661

Related U.S. Application Data
[62] Division of Ser. No. 151,557, June 9, 1971, Pat. No. 3,838,183.

[52] U.S. Cl................ 260/643 R; 203/33; 203/39; 260/640; 260/643 D
[51] Int. Cl.².......................................... C07C 29/26
[58] Field of Search..................... 260/643 D, 643 R

[56] References Cited
UNITED STATES PATENTS
2,042,212  5/1936  Deanesly......................... 260/643 D
2,687,439  8/1954  Garner et al..................... 260/643 D
3,308,173  3/1967  Emrick ........................... 260/643 D
3,737,467  6/1973  Fordham et al. .................. 260/640

FOREIGN PATENTS OR APPLICATIONS
966,634  8/1964  United Kingdom............. 260/643 D
903,609  8/1962  United Kingdom............. 260/643 D

*Primary Examiner*—Joseph E. Evans
*Attorney, Agent, or Firm*—Samuel L. Welt; Jon S. Saxe; Richard A. Gaither

[57] ABSTRACT

A process for producing 2-methyl-3-buten-2-ol by reacting isoprene with a hydrohalide and then with an aqueous base and then distilling the aqueous mixture in the presence of excess base to maintain the reaction mixture during distillation at a pH of at least 4.

4 Claims, No Drawings

SYNTHESIS OF 2-METHYL-3-BUTEN-2-OL

This is a division of application Ser. No. 151,557, filed June 9, 1971, now U.S. Pat. No. 3,838,183.

BACKGROUND OF THE INVENTION

In the past, 2-methyl-3-buten-2-ol (MBE) has been manufactured by first reacting acetylene and acetone and then selectively hydrogenating the resulting 2-methyl-3-butyn-2-ol. This process requires relatively expensive process equipment and raw materials and creates at least one mole of calcium waste (derived from the reaction of water and calcium carbide to give acetylene), per mole of MBE produced by the process. This large amount of waste material gives rise to disposal problems.

An alternative process for manufacturing MBE has been developed which overcomes the aforementioned disabilities in manufacturing MBE from acetylene. This process utilizes isoprene as the starting material and involves the process steps of hydrohalogenation and subsequent solvolysis. See A. J. Ultee, Sr., *Rec. Trav. Chim.*, Volume 68, pages 483–484 (1949) and U.S. Pat. No. 2,382,031. This alternative process requires relatively inexpensive process equipment (e.g., only one reaction vessel being required), relatively inexpensive raw materials, and creates only ½ mole of waste $CaCl_2$ per mole of MBE produced, thereby substantially reducing the disposal problem.

However, the savings realizable from utilizing isoprene rather than acetylene in manufacturing MBE have not been as great as were anticipated. One reason for this is that the yields of MBE from this process have not heretofore proven to be very great. By this process, MBE has heretofore been obtained from isoprene in yields of no greater than about 20 to 50%. The yield of the MBE by this process has been reduced due to the formation of side products such as 2-methyl-4-hydroxy-2-butene (prenol). There has been a need for an improved process for manufacturing MBE from isoprene in relatively high yields i.e., yields about 80% or better.

SUMMARY OF THE INVENTION

In accordance with this invention, it has been discovered that MBE can be obtained in high yields of at least 80% from the addition product of isoprene and a hydrohalide by providing an aqueous solution containing the addition product and a base and distilling the solution while maintaining the solution at a pH of at least 4 to produce a distillate containing MBE. In accordance with another embodiment of this invention, the isoprene is combined with the hydrohalide at a temperature of between 0°C. and −110°C. and at an elevated pressure, and the reactants are combined in such a way that isoprene is added to a reaction mixture containing an initial quantity of isoprene and an excess of added hydrohalide.

DETAILED DESCRIPTION

In accordance with the improved process of this invention, 2-methyl-1,3-butadiene (isoprene) is initially reacted with a hydrohalide such as hydrogen bromide or hydrogen chloride, preferably hydrogen chloride. The resulting addition product comprises principally 2-methyl-2-halo-3-butene (2-halo compound) and/or 2-methyl-4-halo-2-butene (4-halo compound). In carrying out this first step of the process of this invention, the hydrohalide is contacted with the isoprene in a conventional manner, preferably by bubbling the gaseous hydrohalide through liquid isoprene.

A particularly preferred method of carrying out this first reaction step is by providing a reaction mixture containing equimolar quantities of isoprene and hydrohalide. In this procedure, these equimolar quantities are obtained by:

1. introducing, initially, a portion of the isoprene to be reacted, preferably about 10 – 25% by weight into the reaction vessel;

2. adding the hydrohalide into the initially added portion of isoprene until the isoprene is saturated thereby, creating an excess of the added hydrohalide in the initially added portion of the isoprene; and 3. Adding the remaining isoprene and hydrohalide, to be reacted, to the reaction vessel, the rate of addition of the two reactants being such that there is an excess of added hydrohalide. This excess remains until all the isoprene has been added to provide equimolar amounts of the isoprene and the hydrohalide. By this particularly preferred method, the production of waste materials (polymeric and halide containing compounds) formed by the process of this invention is minimized, preferably to about 10%.

In general, this reaction can be carried out at room temperature, i.e., 30°C. and atmospheric pressure, with temperatures of from 0°C. to the freezing point of the hydrohalide and elevated pressures of greater than one atmosphere being preferred. If desired, higher temperatures can be utilized.

In accordance with the preferred embodiment of this invention, it has been found that this reaction proceeds more quickly at low temperatures and at elevated pressures. For example, with vigorous stirring in a closed system, the time for the uptake of HCl for a 2 mole batch requires about 6 hours at 0°C., 2-3 hours at −20°C. and about 20 minutes at −70°C. It has also been found that the ratio of the 2-halo compound to the 4-halo compound increases as the reaction temperature decreases. For example, at 0°C., −20°C., and −70°C., the weight ratios of the 2-halo compound to the 4-halo compound are respectively 50:50, 70:30 and 90:10.

In accordance with a particularly preferred embodiment of this invention, the reaction carried out at −70°C., with vigorous stirring achieves a 95% conversion to the addition product in approximately 1 to 2 hours. The remaining 5% unreacted isoprene can be completely reacted in about 18 hours. In addition, at this temperature, no visible isomerization from the 2-halo to the 4-halo compound is observed in the reaction mixture over a period of 6 hours.

In the second step of the improved process of this invention, the addition product from the reaction between isoprene and the hydrohalide is converted to MBE by adding a base and water to the addition product and then distilling the mixture. This reaction is carried out by adding an excess of base to the addition product of the isoprene and the hydrohalide so that the pH of the reaction mixture is raised to at least 4, preferably at a pH of from 7 to 14. The amount of the "excess base" added in this reaction exceeds the amount of base required to hydrolyze the addition product of the first step, preferably by about 5% to about 35%. In carrying out this second step, it is preferred to add the base and then the water to the addition product of the first step. Any conventional, inexpensive organic or inorganic base such as the alkali metal, ammonium or alkaline earth metal hydroxides, carbonates and bicarbonates, as well as organic bases such as nitrogen containing organic bases, which include tri-lower alkylamines or heterocyclic amine bases, may be utilized in this reaction. Among the preferred inorganic bases are included $Ca(OH_2)$, $CaCO_3$, $NaHCO_3$, $Na_2CO_3$, $NH_4OH$, quinoline, pyridine, triethylamine, etc., with $CaCO_3$ being especially preferred.

The reaction mixture, containing the excess base is then subjected to a conventional distillation operation. This distillation is carried out at a temperature of from 55°C. to 95°C. Distillation at this temperature produces a water-MBE azeotrope as the distillate. The resulting distillate contains water and MBE. The residue remaining from this distillation contains prenol, the base, polymerized isoprene, and other side products.

The addition of base to the addition product of the first step is considered essential in obtaining a high yield of MBE. It has been discovered that the use of the excess base prevents the addition product of the first reaction step from forming side products during formation and distillation.

The MBE in the distillate can be recovered in pure form by any conventional means of drying so as to separate the water from the MBE.

A preferred means for separating the water in the distillate from the MBE is by adding to the distillate a water soluble inorganic salt and an inert water-immiscible organic solvent to form a two-phase system, i.e., a water phase and an organic phase, and after separating the water phase, distilling the solvent from the organic phase to recover pure MBE, while the organic phase is maintained at a pH of at least 4, preferably 7 to 14.

In carrying out this separation, any water immiscible organic solvent can be utilized. Among the preferred solvents are hexane, methylene chloride, benzene and toluene, with hexane being especially preferred. If the solvent has a boiling point lower than the boiling point of the water-MBE azeotrope, the solvent is separated from the MBE by distilling off the solvent from the MBE. If the solvent has a boiling point higher than the MBE water azeotrope, the solvent is separated from MBE by distilling off the MBE.

In carrying out this separation, the inorganic salt should be added in an amount to provide an aqueous solution containing at least 50% by weight of the salt necessary to saturate the water. Generally, it is preferred to add the salt in sufficient amounts to saturate the aqueous solution. It has been found that the addition of inorganic salt inhibits the dissolution of water in the organic solvent phase. In this extraction, any conventional, non-acidic, water soluble, inorganic salt such as the alkali metal halides, preferably sodium chloride can be utilized.

The organic solvent extract is then conventionally, fractionally distilled to separate the MBE therefrom. From this fractional distillation step, the organic solvent removed may contain minor amounts of MBE. The removed solvent can, if desired, be recycled to extract another batch of MBE water distillate. The distillation should be carried out at a pH of at least 4, preferably from 7 to 14. This pH can be obtained by the addition of base to the organic extract. Any of the bases utilized in the first distillation step can be utilized in this fractional distillation step to maintain the pH of the extract to at least 4. On the other hand, some of the base originally present from the first distillation step may be present in this organic extract to provide the necessary pH.

The example which follows further illustrates the improved process of this invention. All temperatures are in degrees Centigrade. The initial 30 g. charge of isoprene consists of:

a. all of the recovered isoprene from the previous batch that is collected in the two dry ice traps and the material boiling up to 55°C. in the first azeotropic distillation (usually 5–9 g.);

b. the entire distillation residue of the drying and purification procedure of the previous batch, the weight of this material usually being 10–20 g. and consisting of prenol and MBE (~ 75%) and impurities (~ 25%); and c. the weight adjusted to 30.0 g. using pure isoprene. Each experiment utilizes a total of 136 g. (2 moles) of fresh and recycled isoprene.

EXAMPLE

For each experiment, into a 1 liter 3-necked flask, equipped with a mechanical stirrer, subsurface gas inlet tube and 250 cc. dropping funnel (with pressure equalizer) carrying an adapter connected to a rubber balloon, is weighed initially 30 g. of isoprene, which includes recovered isoprene, if any, from the previous experiment and/or the distillation residues of the drying and purification procedure of the previous experiment and/or fresh isoprene. The rest of the 136 g. of isoprene for each experiment is put into the dropping funnel, and the system is hermetically closed by attaching the adapter with the rubber balloon on top of the dropping funnel on the one hand and by clamping the tubing coming from the HCl cylinder on the other hand. The flask is almost totally immersed into a dry ice-acetone bath and the contents are stirred for 15 minutes under the vacuum developed in the flask. After the substrates have reached dry ice temperature (−70°C.), 76 g. (2.08 moles) of HCl gas is introduced at a slight overpressure while stirring. After about 30–40 g. of hydrogen chloride has been introduced (ca. 10 minutes), the remaining isoprene is added via the dropping funnel within ca. 20 minutes, while maintaining a strong flow of HCl gas. The addition of hydrogen chloride is finished in approximately 5–10 minutes prior to the end of the isoprene addition. The slightly turbid mixture, when containing a recycle distillation residue from a previous experiment, is then stirred for 1 hour at this temperature, after which time an IR analysis indicates little isoprene (5% by weight remaining).

The cooling bath is then removed. Then, 120 g. of $CaCO_3$ (20% mole excess) and thereafter 300 cc. of water are added to the reaction mixture. The dropping funnel is replaced by an efficient coil condenser (water-cooled) which is connected to dry ice cooling traps. The white heterogenous reaction mixture is then stirred vigorously under cooling. $CO_2$ is evolved in a steady flow and the temperature rises from initially ca. 10°C. to approximately 30°C. After ca. 2 hours, the gas evolution comes to a virtual standstill. A quantity of isoprene, collected in the dry ice traps, is recycled to the next experiment. The reaction mixture is then heated in an oil bath and the MBE is distilled (with stirring) as an azeotrope with water. A forerun, boiling from 25° to 50° C., is collected and combined with the material accumulated in the cooling traps. The main fraction is taken from 55°–95°C., principally from 85°–90°C. About 210 g. of azeotrope is obtained. The aqueous residue, pH ca. 4–6, contains an oily layer consisting mainly of side products, isoprene oligomers and polymers, chlorine-containing compounds, MBE and prenol. The full amount of azeotrope is then diluted with 136 g. of fresh hexane or the hexane forerun of the previous experiment. The precipitated water is saturated with NaCl (15–20 g.) and the layers separated. The water is discarded and the colorless organic phase is transferred to a 1 liter flask and ca. 0.5 g. of $NaHCO_3$ is added. Fractional distillation at atmospheric pressure is carried out using a 30 cm. Vigreux column. The hexane forerun, b.p. 55°–94° C., is recycled to the next experiment after separating ca. 5–10 g. of water. The main distillation fraction is taken at 94°–99° C. and the resulting residue is recycled into the next experiment.

Using the described procedures, an average yield in excess of 80 percent of MBE (based on isoprene) is isolated - see the following table of experiments. The main fractions show a purity of ca. 99 percent.

The table which follows sets forth the data for the experiments 1–9 of the example.

I claim:
1. A process for separating 2-methyl-3-buten-2-ol from an aqueous medium which is an azeotrope of 2-methyl-3-buten-2-ol and water which comprises:
   adding an alkali metal halide and an inert water-immiscible organic solvent to said aqueous medium to form a two-phase system containing an organic phase and an aqueous phase wherein the salt is added to provide at least 50% of the amount necessary to saturate said aqueous phase, separating said aqueous phase from said organic phase and fractionally distilling said organic phase to recover 2-methyl-3-buten-2-ol while maintaining the organic phase at a pH of at least 4.
2. The process of claim 1 wherein said solvent is hexane.
3. The process of claim 1 wherein said alkali metal halide is sodium chloride.
4. The process of claim 1 wherein the salt is provided in an amount sufficient to saturate the aqueous phase.

TABLE OF EXPERIMENTS

| Expt. No. | Isoprene g. | Isoprene Recycle g. | Phenol Recycle g. | HCl g. | $CaCO_3$ g. | Isoprene Recov. g. | Total Azeotrope g. | Polymer Residue g. | NaCl g. | Added Hexane, Forerun g. | $H_2O$ Layer Separated cc. | Hexane Forerun Obtained b.p. 55–94 g. | Main Fraction b.p 94–99 g. | Yield % | Phenol Recycle Residue g. |
|---|---|---|---|---|---|---|---|---|---|---|---|---|---|---|---|
| 1 | 136 | — | — | 76.0 | 125 | 5.0 | 186.9 | 14.2 | 15 | 184.1 | 44 | 195.8 | 120.2 | 70 | 13.8 |
| 2 | 136 | 5.0 | 13.8 | 85.4 | 140 | 6.8 | 209.5 | 14.2 | 15 | 189.1 | 46 | 203.0 | 135.1 | 79 | 16.0 |
| 3 | 136 | 6.8 | 16.0 | 88.5 | 145 | 5.6 | 204.1 | 19.0 | 15 | 193.5 | 46 | 206.4 | 132.5 | 77 | 15.0 |
| 4 | 136 | 5.6 | 15.0 | 86.0 | 142 | 9.8 | 205.0 | 16.6 | 20 | 199.0 | 49 | 196.4 | 145.4 | 85 | 18.6 |
| 5 | 136 | 9.8 | 18.6 | 92.0 | 151 | 7.0 | 218.6 | 17.2 | 20 | 188.9 | 51 | 197.4 | 148.3 | 86 | 16.9 |
| 6 | 136 | 7.0 | 16.9 | 90.0 | 148 | 5.3 | 214.3 | 20.3 | 20 | 188.2 | 49 | 199.2 | 141.3 | 82 | 14.6 |
| 7 | 136 | 5.3 | 14.6 | 89.0 | 148 | 7.2 | 216.2 | 16.9 | 20 | 191.6 | 51 | 186.5 | 151.0 | 88 | 18.7 |
| 8 | 136 | 7.2 | 18.7 | 91.0 | 150 | 7.2 | 215.0 | 18.0 | 20 | 178.1 | 51 | 192.9 | 140.0 | 81 | 14.0 |
| 9 | 136 | 7.2 | 14.0 | 90.0 | 148 | 4.6 | 222.0 | 11.0 | 20 | 185.3 | 52 | 195.5 | 146.6 | 85 | 14.2 |

* * * * *